US007632657B2

(12) United States Patent
Rambach et al.

(10) Patent No.: US 7,632,657 B2
(45) Date of Patent: Dec. 15, 2009

(54) METHOD OF DETECTING METICILLIN-RESISTANT MICROORGANISMS

(75) Inventors: Alain Rambach, 73, boulevard Montparnasse, 75006 Paris (FR); Alain Le Coustumier, Cahors (FR)

(73) Assignee: Alain Rambach, Paris (FR)

( * ) Notice: Subject to any disclaimer, the term of this patent is extended or adjusted under 35 U.S.C. 154(b) by 0 days.

(21) Appl. No.: 10/528,824

(22) PCT Filed: Sep. 23, 2003

(86) PCT No.: PCT/FR03/02788

§ 371 (c)(1),
(2), (4) Date: Mar. 23, 2005

(87) PCT Pub. No.: WO2004/027086

PCT Pub. Date: Apr. 1, 2004

(65) Prior Publication Data

US 2006/0035309 A1 Feb. 16, 2006

Related U.S. Application Data

(60) Provisional application No. 60/413,773, filed on Sep. 27, 2002.

(30) Foreign Application Priority Data

Sep. 23, 2002 (FR) .................................. 02 11718

(51) Int. Cl.
*C12Q 1/18* (2006.01)
(52) U.S. Cl. .................................................... 435/32
(58) Field of Classification Search .................. None
See application file for complete search history.

(56) References Cited

U.S. PATENT DOCUMENTS

| 5,627,045 | A | * | 5/1997 | Bochner et al. | 435/34 |
| 5,650,290 | A | * | 7/1997 | Grant | 435/34 |
| 5,716,799 | A | | 2/1998 | Rambach | |
| 5,882,882 | A | * | 3/1999 | Bochner et al. | 435/34 |
| 5,883,074 | A | * | 3/1999 | Boggs et al. | 514/8 |
| 5,989,853 | A | * | 11/1999 | Bochner et al. | 435/34 |
| 6,130,057 | A | * | 10/2000 | Gosnell et al. | 435/32 |
| 6,221,859 | B1 | * | 4/2001 | Dorso et al. | 514/199 |
| 6,294,527 | B1 | * | 9/2001 | Hanaki et al. | 514/203 |
| 6,436,631 | B1 | * | 8/2002 | Bochner | 435/4 |
| 6,548,268 | B1 | * | 4/2003 | Rambach | 435/34 |
| 6,696,239 | B1 | * | 2/2004 | Bochner | 435/4 |
| 2004/0235012 | A1 | * | 11/2004 | Hammann et al. | 435/6 |

FOREIGN PATENT DOCUMENTS

| EP | 1 543 147 B1 | 6/2005 |
| JP | H0-217760 | 8/1994 |
| JP | H07-000181 | 1/1995 |
| WO | WO 95/04156 | 2/1995 |
| WO | WO 95/20674 | 8/1995 |
| WO | WO 00/53799 | 9/2000 |

OTHER PUBLICATIONS

Merlino J, Leroi M, Bradbury R, Veal D, Harbour C (2000) New chromogenic identification and detection of *Staphylococcus aureus* and methicillin-resistant *S. aureus*. J Clin Microbiol 38: pp. 2378-2380.*

Vouillamoz J et al (2000) *Quinupristin-dalfopristin* combined with beta lactams for treatment of experimental endocarditis due to *S. aureus* constitutively resistant to macrolide-lincosamide-streptogramin B antibiotics. Antimicrob Agents Chemther 44: pp. 1789-1795.*

Aritaka N et al (2001) Combination effect of vancomycin and beta lactams against a *Staphylococcus aureus* strain, Mu3, with heterogeneous resistance to vancomycin. Antimicrob Agents Chemother 45: pp. 1292-1294.*

Felten A et al (Aug. 2002) Evaluation of three techniques for detection of low-level methicillin-resistant *Staphylococcus aureus* (MRSA): a disk diffusion method with cefoxitin and moxalactam, the Vitek 2 system, and the MRSA-screen latex agglutination test. J Clin Microbiol, vol. 40, No. 8, pp. 2766-2771.*

Carricajo A et al (1999) Comparative evaluation of five chromogenic media for detection, enumeration and identification of urinary tract pathogens. Eur J Clin Microbiol Infect Dis, vol. 18, pp. 796-803.*

Pead L et al (1977) *Staphylococci* as urinary pathogens. J Clin Pathol, vol. 30, pp. 427-431.*

Gaillot, O. et al., Evaluation of CHROMagar *Staph. aureus*, a New Chromogenic Medium, for Isolation and Presumptive Identification of *Staphylococcus aureus* from Human Clinical Specimens, J. Clin. Microbiol., 38(4):1587-91 (Apr. 2000).

(Continued)

*Primary Examiner*—Herbert J. Lilling
(74) *Attorney, Agent, or Firm*—Finnegan, Henderson, Farabow, Garrett & Dunner, LLP

(57) ABSTRACT

The invention relates to a novel solid medium for detecting meticillin-resistant micro-organisms, containing an antibiotic selected from the cephalosporin group, particularly second and third generation, and a chromogenic agent bearing a chromophore which is released after hydrolysis with an active enzyme in said micro-organisms.

82 Claims, No Drawings

OTHER PUBLICATIONS

Mougeot, C. et al., *Staphylococcus aureus*: Nouvelle Detection de la Resistance Intrinseque par la Methode de Diffusion, Pathol. Biol., 49:199-204(2001).

Murray, P. R. et al. (eds.), Manual of Clinical Microbiology, 7th Edition, p. 270 (1999).

Tande, D. et al., Interest of Use in Routine of CHROMagar™ MRSA Medium for Detection of Methicillin Resistant *Staphylococcus aureus* Carriers in Intensive Care Unit, (2003).

Manafi, M. et al., Fluorogenic and Chromogenic Substrates Used in Bacterial Diagnostics, Microbiol. Rev., 55:335-48 (Sep. 1991).

Milieux et Reactifs de Laboratoire Pasteur, 3rd Edition (1987).

Felten, A. et al., Performances of 2 Techniques to Detect Low-Level Methicillin Resistant Coagulase Negative *Staphylococci* (LMRCNS): Cephams Disk Diffusion in Agar, Vitek 2 R Automated System, Clin. Microbiol. and Inf., 7:13 (2001).

Wertheim, H. et al., Improved Detection of Methicillin-Resistant *Staphylococcus aureus* Using Phenyl Mannitol Broth Containing Aztreonam and Ceftizoxime, J. Clin. Microbiol., 39:2660-62 (Jul. 2001).

Okonogi, K. et al., Emergence of Methicillin-Resistant Clones from Cephamycin-Resistant *Staphylococcus aureus*, J. Antimicrobial Chemotherapy, 24:637-45 (1989).

Tokue, Y. et al., Comparison of a Polymerase Chain Reaction Assay and a Conventional Microbiologic Mehod for Detection of Methicillin-Resistant *Staphylococcus aureus*, Antimicrob. Agents and Chemotherapy, 36(1):6-9 (Jan. 1992).

Perry, P. L. et al., A Rapid (20h) Solid Screening Medium for Detecting Methicillin-Resistant *Staphylococcus aureus*, J. Hospital Infection, 40:67-72 (1998).

Davies, S., Methicillin-Resistant *Staphylococcus aureus*: Evaluation of Five Selective Media, Br. J. Biomedical Science, 57:269-72 (2000).

Rohrer, S. et al., Improved Methods for Detection of Methicillin-Resistant *Staphylococcus aureus*, Eur. J. Clin. Microbiol. Infect. Dis., 20:267-70 (2001).

Perry, J. D. et al., Evaluation of *S. aureus* ID, a New Chromogenic Agar Medium for Detection of *Staphylococcus aureus*, J. Clin. Microbiol., 41(12):5695-98 (Dec. 2003).

Perry, J. D. et al., Development and Evaluation of a Chromogenic Agar Medium for Methicillin-Resistant *Staphylococcus aureus*, J. Clin. Microbiol., 42(1):4519-23 (Oct. 2004).

Murray, P. R. et al. (eds.), Manual of Clinical Microbiology, 7th Edition, "Antimicrobial Susceptibility Testing: General Considerations." pp. 1469-1473 (1999).

Murray, P. R. et al. (eds.), Manual of Clinical Microbiology, 7th Edition, "Antibacterial Agents," pp. 1474-1504 (1999).

Murray, P. R. et al. (eds.), Manual of Clinical Microbiology, 7th Edition, "Antibacterial Susceptibility Tests: Dilution and Disk Diffusion Methods," pp. 1526-1542 (1999).

Brown, D. "Detection of methicillin/oxacillin resistance in *staphylococci*," Journal of Antimicrobial Chemotheraphy (2001) 48, Suppl S1, 65-70.

Stoakes, L. et al., Prospective Comparison of a New Chromogenic Medium, MRSA*Select*, to CHROMagar MRSA and Mannitol-Salt Medium Supplemented with Oxacillin or Cefoxitin for Detection of Methicillin-Resistant *Staphylococcus aureus*, Journal of Clinical Microbiology, Feb. 2006, pp. 637-639.

Leona W. Ayers et al., "Cefotetan, a New Cephamycin: Comparison of In Vitro Antimicrobial Activity with Other Cephems, B-Lactamase Stability, and Preliminary Recommendations for Disk Duffusion Testing", Antimicrobial Agents and Chemotherapy, 1982, pp. 859-877, vol. 22, No. 5.

Ronald N. Jones et al., "In Vitro Antimicrobial Activity Evaluation of Cefodizime (HR221), a New Semisynthetic Cephalosporin", Antimicrobial Agents and Chemotherapy, Dec. 1981, p. 760-768, vol. 20, No. 6.

Jan Kluytmans et al., "Performance of CHROMagar Selective Medium and Oxacillin Resistance Screening Agar Base for Identifying *Staphylococcus aureus* and Detecting Methicillin Resistance", Journal of Clinical Microbiology, Jul. 2002, pp. 2480-2482, vol. 40, No. 7.

Database WPI, Section Ch, Week 199511, Derwent Publications Ltd., London, GB; Class B04, AN 1995-077141, XP002243919 & JP 07 000181 A (Kyokuto Seiyaku Kogyo KK), Jan. 6, 1995 abrege.

John Merlino et al., "New Chromogenic Identification and Detection of *Staphylococcus aureus* and Methicillin-Resistant *S. aureus*", Journal of Clinical Microbiology, Jun. 2000, pp. 2378-2380, vol. 38, No. 6.

Moriyasu, Iichiro, et al., Multi-Center Evaluation of Showa Ceftizoxime Disk Susceptibility Test to Discriminate between the Strains of Methicillin-Resistant *Staphylococcus aureus* (MRSA) and Those Susceptible (MSSA), pp. 271-277, Jpn J. Clin Pathol, 1994.

Minutes of Hearing in Opposition Proceeding for EP-B-1543147 dated Feb. 25, 2009.

Decision of the Opposition Division in Opposition Proceeding for EP-B-1543147 dated Feb. 26, 2009.

Murray, P.R., et al. (eds.), Manual of Clinical Microbiology, 7th Edition, *Staphylococcus* and *Micrococcus*, pp. 264-277 (1999).

Cavassini, M. et al., "Evaluation of MRSA-Screen, a Simple Anti-PbP 2a Slide Latex Agglutination Kit, for Rapid Detection of Methicillin Resistance in *Staphylococcus aureus*," Journal of Clinical Microbiology, vol. 37, No. 5, May, 1999, pp. 1591-1594.

Kobayashi, N., et al., "Detection of *mecA, femA,* and *femB* genes in clinical strains of *staphylococci* using polymerase chain reaction," Epidemiol. Infect., vol. 113, 1994, pp. 259-266.

Merlino, J., et al., "Detection and expression of methicillin/oxacillin resistance in multidrug-resistant and non-multidrug-resistant *Staphylococcus aureus* in Central Sydney, Australia," Journal of Antimicrobial Chemotherapy, vol. 49, May 2002, pp. 793-801.

Kosmidis, J., et al., "Cefoxitin, a New Semi-synthetic Cephamycin: An In-vitro and In-vivo Comparison with Cephalothin," British Medical Journal, vol. 15, Dec. 1973, pp. 653-655.

Kojo, H., et al., "Antibacterial Activity of Ceftizoxime (FK 749), a New Cephalosporin, Against Cephalosporin-Resistant Bacteria, and Its Stability to β-Lactamase," Antimicrobial Agents and Chemotherapy, vol. 16, No. 5, Nov. 1979, pp. 549-553.

Lang, Selwyn D.R., et al., "Comparison of Cefoperazone. Cefotaxime, and Moxalactam (LY127935) Against Aerobic Gram-Negative Bacilli," Antimicrobial Agents and Chemotherapy, vol. 17, No. 3, Mar. 1980, pp. 488-493.

Neu, Harold C., et al., "In Vitro Activity and β-Lactamase Stability of a New Difluoro Oxacephem, 6315-S, Antimicrobial Agents and Chemotherapy," vol. 30, No. 5, Nov. 1986, pp. 638-644.

Public Health Agency of Canada, "Guidelines for the Testing and Reporting of Antimicrobial Susceptibilities of Methicillin Resistant *Staphylococcus aureus* (MRSA) and Commentary on Methicillin Resistant Coagulase Negative *Staphylococci* (MR-CNS)," Canadian External Quality Assessment Advisory Group for Antibiotic Resistance, Sep. 1998.

Apfaltar, Petra, et al., "Performance of a new chromogenic oxacillin resistance screen medium (Oxoid) in the detection and presumptive identification of methicillin-resistant *Staphylococcus aureus*," Diagnostic Microbiology and Infectious Disease, vol. 44, (2002), pp. 209-211.

Hanaki, Hideaki et al., "TOC-39, a Novel Parenteral Broad-Spectrum Cephalosporin with Excellent Activity against Methicillin-Resistant *Staphylococcus aureus*," Antimicrobial Agents and Chemotheraphy, vol. 39. No. 5, May 1995. pp. 1120-1126.

Lally, Richard T., "Evaluation of Mannitol Salt Agar with Oxacillin as a Screening Medium for Methicillin-Resistant *Staphylococcus aureus*," Journal of Clinical Microbiology, vol. 22, No. 4, Oct. 1985, pp. 501-504.

"Evaluation of a New Medium, Oxacillin Resistance Screening Agar Base, for the Detection of Methicillin-Resistant *Staphylococcus aureus* from Clinical Specimens," Journal of Clinical Microbiology, vol. 39, No. 9. Sep. 2001, p. 3422.

Van Enk, Richard A., et al., "Use of a Primary Isolation Medium for Recovery of Methicillin-Resistant *Stphylococcus aureus*," Journal of Clinical Microbiology, vol. 30, No. 2, Feb. 1992, p. 504-505.

BD BBL™ CHROMagar™ *Staph aureus* product leaflet, © 2005.

Drew et al., "Reliability of the Kirby-Bauer Disc Diffusion Method for Detecting Methicillin-Resistant Strains of *Staphylococcus aureus*," Applied Microbiology, 24(2):240-47 (1972).

Hiramatsu et al., "Molecular Cloning and Nucleotide Sequence Determination of the Regulator Region of *mecA* Gene in Methicillin-Resistant *Staphylococus aureus* (MRSA)," FEBS Letters, 298(23):133-136 (1992).

Joffin et al., Microbiology Technique—vol. 1, Dictionary of Techniques, 3$^{rd}$ Ed., pp. 16-19, 24, 57-60, 140-147, CRDP d'Aquitaine (2001).

Jorgensen et al., "Performance Standards for Antimicrobial Disk Susceptibility Tests—Sixth Edition; Approved Standard," NCCLS document M2-A6 (ISBN 1-56238-308-6), 17(1) (1997).

Jorgensen et al., "Methods for Dilution Antimicrobial Susceptibility Tests for Bacteria That Grow Aerobically—Fourth Edition; Approved Standard," NCCLS document M7-A4 (ISBN 1-56239-309-4), 17(2) (1997).

Murakami et al., "Increased Susceptibility to Cephamycin-Type Antibiotics of Methicillin-Resistant *Staphylococcus aureus* Defective in Penicillin-Binding Protein 2," Antimicrobial Agents and Chemotherapy, 31(9):1423-24 (1987).

Rowe et al., "Agar Diffusion, Agar Dilution, Etest®, and Agar Screening Test in the Detection of Methicillin Resistance in *Staphylococci*," Diagnostic Microbiology and Infectious Disease, 43(1):45-48 (2002).

Sakoulas et al., "Methicillin-Resistant *Staphylococcus aureus*: Comparison of Susceptibility Testing Methods and Analysis of *mecA*-Positive Susceptible Strains," Journal of Clinical Microbiology, 39(11):3946-51 (2001).

\* cited by examiner

METHOD OF DETECTING METICILLIN-RESISTANT MICROORGANISMS

This is a national stage application under 35 U.S.C. §371 of international application PCT/FR03/002788 filed Sep. 23, 2003, which claims priority benefit of French Application No. 0211718 filed Sep. 23, 2002, which are incorporated by reference herein.

The invention relates to a novel gelled medium for detecting meticillin-resistant microorganisms, containing an antibiotic chosen from the cephalosporin group, in particular second or third generation cephalosporins, and a chromogenic agent bearing a chromophore that is released after hydrolysis with an enzyme that is active in said microorganisms.

The systematic detection of meticillin (also written methicillin) resistant *Staphylococcus aureus* (MRSA) is important.

In fact, although MRSAs do not appear to be more virulent than MSSAs (meticillin-sensitive *Staphylococcus aureus*), infections therewith are more difficult and expensive to treat. This is due to the fact that the meticillin resistance confers resistance to all the beta-lactams and that this resistance is very often associated with resistances to many other major anti-Staphylococcal antibiotics (Lyon and Skurry, Microbiol. Rev. 51; 88-134).

Meticillin-supplemented agar growth media have sometimes been used for this detection. This method is now often abandoned since it detects certain MRSA strains poorly, in particular heterogeneous strains in which bacterial populations contain a very low proportion of bacteria absolutely resistant to meticillin (in which one bacterium out of $10^4$ or $10^8$ expresses the resistance). This method gives a high number of false-negative results.

The use of agar growth media supplemented with oxacillin is common but, as with meticillin, certain strains are difficult to detect.

In addition, in order for these antibiotics (meticillin, oxacillin) to function more or less effectively as selective supplements, only certain growth media can be used. Consequently, the media proposed to the user are, for example, derivatives of Muller Hinton Agar or of Mannitol Salt Agar. Unfortunately, for the user, these media are often relatively non-discriminating for the *S. aureus* species, which further decreases the sensitivity and the specificity.

Agar growth media supplemented with tobramycin or ofloxacin have been proposed, either in relatively non-discriminating bases (derived from Mannitol salt Agar, for example) or in the very discriminating CHROMagar *Staph aureus* base, but the correlation with meticillin resistance is mediocre, hence an excess of false positives and of false negatives.

The agar diffusion method, for example using Mueller Hinton agar, is also used, which consists in depositing paper discs impregnated with antibiotics onto an agar seeded with the bacterium to be studied. An antibiotic concentration gradient is established in the agar, around each disc. After incubation, an inhibition halo occurs around each disc, which makes it possible to measure a diameter, which reflects the value of the MIC (minimum inhibitory concentration, minimum concentration for which no microorganism growth is detected).

The present invention relates to an agar culture medium for detecting meticillin-resistant microorganisms, and in particular Staphylococci, especially *Staphylococcus aureus*, with good sensitivity and good specificity.

Thus, in the context of the present invention, use is made of the discriminating capacities of chromogenic media, in combination with the properties of antibiotics of the family of $2^{nd}$ or $3^{rd}$ generation cephalosporins, which make it possible to detect meticillin-resistant microorganisms.

The invention therefore relates to a medium for detecting meticillin-resistant microorganisms, comprising, besides nutrients for the growth of said microorganisms, at least one antibiotic chosen from the group of second or third generation cephalosporins, and a chromogenic agent that releases a chromophore after hydrolysis with an enzyme that is active in said microorganisms.

The culture media according to the invention allow direct detection of the meticillin-resistant microorganisms, because of their growth on the medium according to the invention and of the presence of the chromogenic agent(s), making it possible to define the nature of the microorganism. There is therefore no need for an additional step to confirm the nature of the microorganisms growing on the medium according to the invention.

The media according to the invention make it possible to detect meticillin-resistant bacteria using an inoculum streaked on a dish, whereas the majority of the methods of the prior art use a deposit of approximately $10^4$ to $10^5$ bacteria on the agar. The media according to the invention can be used directly from a sample from a patient, or after an enriching phase.

The expression "second or third generation cephalosporin" is intended to denote the antibiotics of the cephalosporin family having a formula derived from formula (I) below:

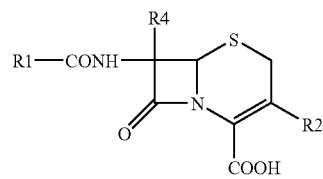

in which R2 is an H group, an acetoxymethyl group, a methylthiotetrazol group, a dimethylaminoethylthio-tetrazol group, a triazine group, an acetaminopyridine (pyridinium) group, or a pyridinium group substituted with a carbamoyl group, a cyclopentopyridinium group or a thiomethylacetoxythiazol group, R1 is an amino-2-thiazole heterocycle, an α-piperazinedione or an α-sulfophenyl, and R4 is an H group or an α-methoxy radical.

In particular, the compounds having the formula below:

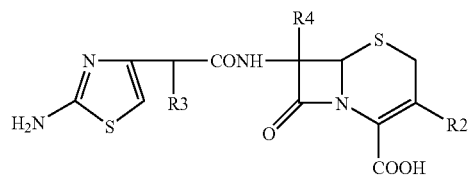

in which R3 is an H group or an α-methoxyimino group, are intended to be denoted.

In a particular case, the R4 group is a hydrogen.

Cephamycins are compounds in which the R4 group is an α-methoxy radical, protecting the β-lactam ring against hydrolysis by β-lactamases, and correspond to the formula below:

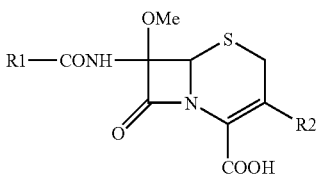

Oxacephems are compounds in which the sulfur atom of the cephem ring is replaced with an oxygen atom, and are considered to be derivatives of formula (I) given above.

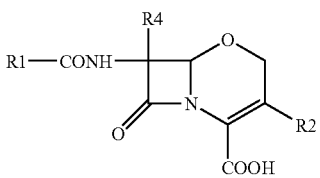

In general, for these compounds, the R4 group is an α-methoxy.

A definition of the cephalosporins thus envisioned can be found in Binger (Mécanisme d'Action des Bêta-lactamines, (de la structure bactérienne à la structure de la molecule) [Mechanism of action of beta-lactams (from bacterial structure to the structure of the molecules], 1986, Roussel (Paris) publisher, chapter III, pages 47-62, and chapter IV, pages 63-68), and in the work by Richmond (Beta-lactam antibiotics (the background to their use as therapeutic aents), Hoechst Aktiengesellschaft, D-6230 Frankfurt (Main) 80 publisher, 1981, chapter 3, pages 55-65).

In a secondary capacity, it may be noted that second generation cephalosporins exhibit a better effect than first generation cephalosporins against Gram-negative bacteria, and show better resistance to degradation by β-lactamases, third generation cephalosporins having an even broader effect spectrum with respect to Gram-negative bacteria.

Among the second and third generation cephalosporins, mention may be made of: loracarbef, cefaclor, cefuroxime, cefprozil, cefoxitin (cefoxitan), cefamandole, cefotian, cefotetan, cefmetazole, cefocinide, ceforanide, cefpodoxime, cefixime, cefotaxime, ceftizoxime, ceftriaxone, ceftazidime, cefmenoxime, cefodizime, cefoperazone, cefepime, cefpirome, cefsulfonide, cefetamete, ceftibutene, moxalactam, latamoxef and flomoxef, in particular in the form of salts (sodium salts). Those skilled in the art can obtain lists of such compounds, in particular on the internet at the site www.biam2.org or www.fpnotebook.com.

In a preferred embodiment, said antibiotic is cefamandole.

In another embodiment, said antibiotic is chosen from the group of cephamycins (cefoxitin, cefotetan, cefmetazole, cefbutperazone, cefminox) and of oxacephems (moxalactam, latamoxef or flomoxef).

In a preferred embodiment, said antibiotic is cefoxitin.
In a preferred embodiment, said antibiotic is cefmetazole.
In a preferred embodiment, said antibiotic is moxalactam.
In a preferred embodiment, said antibiotic is cefotetan.

The concentration of antibiotic in the medium according to the invention is preferably between 0.5 and 50 mg/l, preferably 1.5 and 30 mg/l, in particular 1.5 and 15 mg/l. A few routine tests enable those skilled in the art to adjust this as a function of the MIC (minimum inhibitory concentration, minimum concentration for which no microorganism growth is detected) with respect to the microorganisms under consideration, for the antibiotic under consideration. It should be noted that, among the antibiotics capable of forming part of the composition of a medium of the invention, some are capable of conferring certain properties on said medium. For example, cefoxitin or cefmetazole confer a specific stability, of at least 2 months, on said medium.

For example, a stability of at least 2 months has been observed for a medium in accordance with the invention prepared with cefoxitin at a concentration of 5 mg/l, added to the medium when the latter is at a temperature of 48° C. The stability of the medium in accordance with the invention has been brought to at least 5 months when said medium has been prepared with cefmetazole at a concentration of 2.5 mg/l, added to the medium when the latter is at a temperature of 48° C.

The expression "stability of the medium" is intended to denote the ability of the medium in accordance with the invention to allow the selective detection of meticillin-resistant microorganisms, in particular staphylococcus aureus, for a given period of time, with the same reliability throughout the period of time.

It should also be noted that another cephalosporin, flomoxef, exhibits, for its part, the ability to conserve its antibiotic activity when it is subjected to a temperature of greater than 100° C. (its resistance having even been verified by the inventors at 121° C.).

Such a property makes it possible to produce a medium in accordance with the invention in the form of a single powder, which considerably limits the manipulations that have to be carried out under sterile conditions for the preparation of any culture medium. The flomoxef can therefore be incorporated into the medium being prepared, before heating, which facilitates the preparation thereof. This advantage is not insignificant since it is capable of facilitating the task of any individual having to prepare such media, whatever their experience in the field.

In a preferred embodiment, said microorganisms are staphylococci, and a chromogenic agent chosen from the group consisting of 5-bromo-6-chloro-3-indoxyl phosphate and 5-bromo-4-chloro-3-indoxyl glucoside, as described in application WO 00/53799, is preferably used.

S. aureus culture media are known and described in particular in the manual "Oxoïd Unipath Limited", Wade Road, Basingstoke, Hampshire, RG24 0PW, England. It may for example be "Nutrient Agar Oxoïd CM3", a medium essentially based on yeast extracts, on, peptone and on agar.

In a preferred embodiment, said culture medium contains both 5-bromo-6-chloro-3-indoxyl phosphate and 5-bromo-4-chloro-3-indoxyl glucoside.

The media according to the present invention will preferably contain from 0.01 to 0.50 g/l, in particular from 0.05 to 0.40 g/l of 5-bromo-6-chloro-3-indoxyl phosphate, preferably from 0.01 to 0.20 g/l of 5-bromo-4-chloro-3-indoxyl glucoside, preferably from 0.01 to 0.20 g/l of 5-bromo-4-chloro-3-indoxyl galactoside, preferably from 0.01 to 0.20 g/l of 5-bromo-4-chloro-3-indoxyl glucuronide.

In a particular embodiment, the culture medium according to the invention also comprises at least one of the following two chromogenic agents: 5-bromo-4-chloro-3-indoxyl galactoside and 5-bromo-4-chloro-3-indoxyl glucuronide.

In a particular embodiment, said medium also contains deferoxamine. Deferoxamine in fact makes it possible to inhibit *Staphylococcus epidermis* without inhibiting *Staphylococcus aureus*, and the concentration used will preferably be between 0.01 and 0.10 g/l.

In one embodiment, the medium according to the invention also contains a glycopeptide antibiotic chosen from the group consisting of vancomycin, teicoplanin and avoparcin, and mixtures thereof, in order to detect microorganisms resistant both to meticillin and to vancomycin. Approximately from 5 mg/l to 50 mg/l of these antibiotics, more particularly from 5 mg/l to 30 mg/l, from 10 mg/l to 30 mg/l, and approximately 25 mg/l, can be used.

In the context of the present invention, the inventors have shown that it is not necessary to have a high osmotic load in the culture medium. Thus, unlike the media for detecting meticillin-resistant *Staphylococcus aureus* using oxacillin as antibiotic, to which sodium chloride is added, the culture medium of the invention is also functional with a sodium concentration of less than 3%, and equal to approximately 2-2.5%. The incubation conditions can be adjusted according to the amount of sodium chloride in the medium (incubation time, higher or lower temperature, etc.).

The invention also relates to the use of a medium according to the invention, for detecting meticillin-resistant microorganisms.

The invention also relates to a method of detecting meticillin-resistant microorganisms in a sample, comprising the steps consisting in:
- inoculating a medium according to the invention with said sample or an inoculum derived from said sample,
- incubating said medium under conditions that allow growth of said microorganisms,
- detecting, on said medium, the presence of said meticillin-resistant microorganisms by virtue of the presence of colored colonies.

The incubation conditions are known to those skilled in the art, and an incubation at temperatures of between 25° C. and 42° C., preferably between 30° C. and 38° C., is generally used.

The incubation times are conventional (approximately 24 hours).

According to the microorganism under consideration, it is possible to use a shorter or longer incubation time, to work under aerobic or anaerobic conditions, etc.

The medium according to the invention makes it possible in particular to readily detect meticillin-resistant staphylococci, while reducing the analysis time. The combination of the antibiotics chosen in the context of the invention and of the chromogenic agents in fact makes it possible to reduce the number of false positives and of false negatives, and to thus reduce the need for carrying out supplementary analyses.

EXAMPLES

Example 1

Composition of a medium according to the invention for detecting meticillin-resistant *S. aureus*:
Peptone and yeast extract 40 g/l
NaCl 25 g/l
5-bromo-6-chloro-3-indoxyl phosphate 0.10 g/l
5-bromo-4-chloro-3-indoxyl glucoside 0.05 g/l
5-bromo-4-chloro-3-indoxyl galactoside 0.05 g/l
5-bromo-4-chloro-3-indoxyl glucuronide 0.05 g/l
Deferoxamine 0.050 g/l
Agar 15 g/l
Oxacillin (6 mg/ml) or cefoxitin (5 mg/l) are added to this medium, after autoclaving, before the medium is solid (when it is at a temperature of approximately 45° C.)

This medium contains 5-bromo-6-chloro-3-indoxyl phosphate and 5-bromo-4-chloro-3-indoxyl glucoside, allowing the specific detection of *Staphylococcus aureus* (purple coloration of the colonies), and also 5-bromo-4-chloro-3-indoxyl galactoside and 5-bromo-4-chloro-3-indoxyl glucuronide, in order to color the other microorganisms which may be present in the inoculum.

Example 2

Study of the growth of meticillin-resistant *S. aureus* strains on CHROMagar Staph aureus medium (available from the company CHROMagar, 4, Place du 18 Juin 1940, 75006 Paris France):
AR4295 MetiS: meticillin-sensitive strain
AR4297 MetiR: (homogeneous) meticillin-resistant strain
MRhet: (heterogeneous) meticillin-resistant strain
Z252: meticillin-resistant strain, homogeneous, low level of resistance

|  | AR4295 MetiS | AR4297 MetiR | MRhet | Z252 |
| --- | --- | --- | --- | --- |
| CHROMagar Staph aureus | + | + | + | + |
| CHROMagar Staph aureus + oxacillin 6 mg/ml | − | +/−* | − | − |
| CHROMagar Staph aureus + Cefoxitin 5 mg/l | − | + | + | + |

+ = colony growth;
− = no growth;
* = microcolonies

Petri dishes are inoculated with bacterial cultures by streaking the dishes, in order to observe the growth of isolated bacteria, after incubation at 37° C. for 24 hours.

The bacteria that grow give purple colonies on the culture medium, confirming that the microorganisms are *Staphylococcus aureus*.

Thus, the medium according to the invention makes it possible to directly detect meticillin-resistant *Staphylococcus aureus*, including the heterogeneous strains or the strains with a low level of resistance, due to the combination of bacterial growth and of colony coloration.

The invention claimed is:

1. A solid culture medium for detecting methicillin-resistant *Staphylococcus aureus* (MRSA), comprising:
   nutrients for the growth of said *Staphylococcus aureus*;
   an antibiotic added to the medium before the medium is solid, wherein the antibiotic is cefoxitin, cefmetazole, or moxalactam; and
   a chromogenic agent that releases a chromophore after hydrolysis with an enzyme that is active in said MRSA.

2. The solid culture medium of claim 1, wherein the chromogenic agent is 5-bromo-6-chloro-3-indoxyl-phosphate.

3. The solid culture medium of claim 2, wherein the concentration of the 5-bromo-6-chloro-3-indoxyl-phosphate is from 0.01 to 0.50 g/l.

4. The solid culture medium of claim 3, wherein the concentration of the 5-bromo-6-chloro-3-indoxyl-phosphate is from 0.05 to 0.40 g/l.

5. The solid culture medium of claim 2, further comprising 5-bromo-4-chloro-3-indoxyl glucoside.

6. The solid culture medium of claim 5, wherein the concentration of the 5-bromo-4-chloro-3-indoxyl glucoside is from 0.01 to 0.20 g/l.

7. The solid culture medium of claim 1, further comprising at least one of 5-bromo-4-chloro-3-indoxyl galactoside or 5-bromo-4-chloro-3-indoxyl glucuronide.

8. The solid culture medium of claim 7, wherein the concentration of the 5-bromo-4-chloro-3-indoxyl galactoside is from 0.01 to 0.20 g/l.

9. The solid culture medium of claim 7, wherein the concentration of the 5-bromo-4-chloro-3-indoxyl glucuronide is from 0.01 to 0.20 g/l.

10. The solid culture medium of claim 1, wherein the medium comprises agar.

11. The solid culture medium of claim 1, comprising sodium chloride at a concentration of less than 3%.

12. The solid culture medium of claim 1, wherein the antibiotic is cefoxitin.

13. The solid culture medium of claim 1, wherein the antibiotic is cefmetazole.

14. The solid culture medium of claim 1, wherein the antibiotic is moxalactam.

15. The solid culture medium of claim 1, wherein the concentration of antibiotic is between 0.5 and 50 mg/l.

16. The solid culture medium of claim 1, further comprising vancomycin, teicoplanin, avoparcin, or a mixture thereof.

17. The solid culture medium of claim 16, wherein the concentration of vancomycin, teicoplanin, avoparcin, or a mixture thereof is between approximately 5 mg/l to 50 mg/l.

18. The solid culture medium of claim 1, wherein the antibiotic is cefoxitin and the chromogenic agent is 5-bromo-6-chloro-3-indoxyl-phosphate.

19. The solid culture medium of claim 1, wherein the antibiotic is cefmetazole and the chromogenic agent is 5-bromo-6-chloro-3-indoxyl-phosphate.

20. The solid culture medium of claim 1, further comprising deferoxamine.

21. A solid culture medium for detecting methicillin-resistant *Staphylococcus aureus* (MRSA), comprising:
nutrients for the growth of said *Staphylococcus aureus*;
an antibiotic added to the medium before the medium is solid, wherein the antibiotic is flomoxef; and
a chromogenic agent that releases a chromophore after hydrolysis with an enzyme that is active in said MRSA.

22. The solid culture medium of claim 21, wherein the chromogenic agent is 5-bromo-6-chloro-3-indoxyl-phosphate.

23. The solid culture medium of claim 22, wherein the concentration of the 5-bromo-6-chloro-3-indoxyl-phosphate is from 0.01 to 0.50 g/l.

24. The solid culture medium of claim 23, wherein the concentration of the 5-bromo-6-chloro-3-indoxyl-phosphate is from 0.05 to 0.40 g/l.

25. The solid culture medium of claim 22, further comprising 5-bromo-4-chloro-3-indoxyl glucoside.

26. The solid culture medium of claim 25, wherein the concentration of the 5-bromo-4-chloro-3-indoxyl glucoside is from 0.01 to 0.20 g/l.

27. The solid culture medium of claim 21, further comprising at least one of 5-bromo-4-chloro-3-indoxyl galactoside or 5-bromo-4-chloro-3-indoxyl glucuronide.

28. The solid culture medium of claim 27, wherein the concentration of the 5-bromo-4-chloro-3-indoxyl galactoside is from 0.01 to 0.20 g/l.

29. The solid culture medium of claim 21, wherein the concentration of the 5-bromo-4-chloro-3-indoxyl glucuronide is from 0.01 to 0.20 g/l.

30. The solid culture medium of claim 21, wherein the medium comprises agar.

31. The solid culture medium of claim 21, comprising sodium chloride at a concentration of less than 3%.

32. The solid culture medium of claim 21, wherein the concentration of flomoxef is between 0.5 and 50mg/l.

33. The solid culture medium of claim 21, further comprising vancomycin, teicoplanin, avoparcin, or a mixture thereof.

34. The solid culture medium of claim 33, wherein the concentration of vancomycin, teicoplanin, avoparcin, or a mixture thereof is between approximately 5 mg/l to 50 mg/l.

35. The solid culture medium of claim 21, further comprising deferoxamine.

36. A method of detecting the presence or absence of methicillin-resistant *Staphylococcus aureus* (MRSA) in a sample from a patient, comprising:
(a) inoculating a solid medium comprising (i) nutrients for the growth of said MRSA; (ii) an antibiotic, wherein the antibiotic is cefoxitin, cefmetazole, or moxalactam, and wherein the antibiotic is added to the medium before the medium is solid; and (iii) a chromogenic agent that releases a chromophore after hydrolysis with an enzyme that is active in said MRSA, with said sample;
(b) incubating said medium under conditions that allow growth of said MRSA;
(c) detecting, on said medium, the presence or absence of said MRSA by virtue of the presence or absence of colored colonies.

37. The method of claim 36, wherein the sample is inoculated directly from a patient.

38. The method of claim 36, wherein the sample is inoculated after an enriching phase.

39. The method of claim 36, wherein the sample is inoculated by streaking onto the medium.

40. The method of claim 36, wherein the chromogenic agent is 5-bromo-6-chloro-3-indoxyl-phosphate.

41. The method of claim 40, wherein the concentration of the 5-bromo-6-chloro-3-indoxyl-phosphate is from 0.01 to 0.50 g/l.

42. The method of claim 41, wherein the concentration of the 5-bromo-6-chloro-3-indoxyl-phosphate is from 0.05 to 0.40 g/l.

43. The method of claim 36, wherein the medium further comprises 5-bromo-4-chloro-3-indoxyl glucoside.

44. The method of claim 43, wherein the concentration of the 5-bromo-4-chloro-3-indoxyl glucoside is from 0.01 to 0.20 g/l.

45. The method of claim 36, wherein the medium further comprises at least one of 5-bromo-4-chloro-3-indoxyl galactoside or 5-bromo-4-chloro-3-indoxyl glucuronide.

46. The method of claim 45, wherein the concentration of the 5-bromo-4-chloro-3-indoxyl galactoside is from 0.01 to 0.20 g/l.

47. The method of claim 45, wherein the concentration of the 5-bromo-4-chloro-3-indoxyl glucuronide is from 0.01 to 0.20 g/l.

48. The method of claim 36, wherein the medium comprises agar.

49. The method of claim 36, wherein the medium comprises sodium chloride at a concentration of less than 3%.

50. The method of claim 36, wherein the antibiotic is cefoxitin.

51. The method of claim 36, wherein the antibiotic is cefmetazole.

52. The method of claim 36, wherein the antibiotic is moxalactam.

53. The method of claim 36, wherein the concentration of antibiotic is between 0.5 and 50 mg/l.

54. The method of claim 36, wherein the medium further comprises vancomycin, teicoplanin, avoparcin, or a mixture thereof.

55. The method of claim 54, wherein the concentration of vancomycin, teicoplanin, avoparcin, or a mixture thereof is between approximately 5 mg/l to 50 mg/l.

56. The method of claim 36, wherein the antibiotic is cefoxitin and the chromogenic agent is 5-bromo-6-chloro-3-indoxyl-phosphate.

57. The method of claim 36, wherein the antibiotic is cefmetazole and the chromogenic agent is 5-bromo-6-chloro-3-indoxyl-phosphate.

58. The method of claim 36, wherein the medium further comprises deferoxamine.

59. The method of claim 36, wherein the incubation is at a temperature between 25° C. and 42° C.

60. The method of claim 59, wherein the incubation is at a temperature between 30° C. and 38° C.

61. The method of claim 60, wherein the incubation is at a temperature of 37° C.

62. A method of detecting the presence or absence of methicillin-resistant *Staphylococcus aureus* (MRSA) in a sample from a patient, comprising:
  (a) inoculating a solid medium comprising (i) nutrients for the growth of said MRSA; (ii) an antibiotic wherein the antibiotic is flomoxef, and wherein the antibiotic is added to the medium before the medium is solid; and (iii) a chromogenic agent that releases a chromophore after hydrolysis with an enzyme that is active in said MRSA, with said sample;
  (b) incubating said medium under conditions that allow growth of said MRSA;
  (c) detecting, on said medium, the presence or absence of said MRSA by virtue of the presence or absence of colored colonies.

63. The method of claim 62, wherein the sample is inoculated directly from a patient.

64. The method of claim 62, wherein the sample is inoculated after an enriching phase.

65. The method of claim 62, wherein the sample is inoculated by streaking onto the medium.

66. The method of claim 62, wherein the chromogenic agent is 5-bromo-6-chloro-3-indoxyl-phosphate.

67. The method of claim 66, wherein the concentration of the 5-bromo-6-chloro-3-indoxyl-phosphate is from 0.01 to 0.50 g/l.

68. The method of claim 67, wherein the concentration of the 5-bromo-6-chloro-3-indoxyl-phosphate is from 0.05 to 0.40 g/l.

69. The method of claim 62, wherein the medium further comprises 5-bromo-4-chloro-3-indoxyl glucoside.

70. The method of claim 69, wherein the concentration of the 5-bromo-4-chloro-3-indoxyl glucoside is from 0.01 to 0.20 g/l.

71. The method of claim 62, wherein the medium further comprises at least one of 5-bromo-4-chloro-3-indoxyl galactoside or 5-bromo-4-chloro-3-indoxyl glucuronide.

72. The method of claim 71, wherein the concentration of the 5-bromo-4-chloro-3-indoxyl galactoside is from 0.01 to 0.20 g/l.

73. The method of claim 71, wherein the concentration of the 5-bromo-4-chloro-3-indoxyl glucuronide is from 0.01 to 0.20 g/l.

74. The method of claim 62, wherein the medium comprises agar.

75. The method of claim 62, wherein the medium comprises sodium chloride at a concentration of less than 3%.

76. The method of claim 62, wherein the concentration of flomoxef is between 0.5 and 50mg/l.

77. The method of claim 62, wherein the medium further comprises vancomycin, teicoplanin, avoparcin, or a mixture thereof.

78. The method of claim 77, wherein the concentration of vancomycin, teicoplanin, avoparcin, or a mixture thereof is between approximately 5 mg/l to 50 mg/l.

79. The method of claim 62, wherein the medium further comprises deferoxamine.

80. The method of claim 62, wherein the incubation is at a temperature between 25° C. and 42° C.

81. The method of claim 80, wherein the incubation is at a temperature between 30° C. and 38° C.

82. The method of claim 81, wherein the incubation is at a temperature of 37° C.

* * * * *